United States Patent [19]

Quantrille et al.

[11] Patent Number: 4,837,079
[45] Date of Patent: Jun. 6, 1989

[54] ANTIMICROBIALLY ACTIVE, NON-WOVEN WEB USED IN A WET WIPER

[75] Inventors: Thomas E. Quantrille, Blacksburg, Va.; Dale H. Johnson, Rockford, Mich.

[73] Assignee: James River Corporation, Richmond, Va.

[21] Appl. No.: 242,421

[22] Filed: Sep. 9, 1988

[51] Int. Cl.$^4$ .................................................. D04H 1/58
[52] U.S. Cl. ................................. 428/288; 15/104.93; 427/389.9; 427/421; 427/428; 428/290; 428/913
[58] Field of Search ....................... 428/288, 290, 913; 427/389.9, 421, 428; 15/104.93

[56] References Cited

U.S. PATENT DOCUMENTS

| | | |
|---|---|---|
| 4,111,922 | 9/1978 | Beede et al. . |
| 4,311,479 | 1/1982 | Fenn et al. . |
| 4,401,712 | 8/1983 | Morrison . |
| 4,478,821 | 10/1984 | Carrillo . |
| 4,615,937 | 10/1986 | Bouchette . |
| 4,643,180 | 2/1987 | Feld et al. . |
| 4,643,181 | 2/1987 | Brown . |
| 4,655,756 | 4/1987 | Fawkes . |
| 4,692,374 | 9/1987 | Bouchette . |

FOREIGN PATENT DOCUMENTS

WO86/02001  4/1986  PCT Int'l Appl. .

*Primary Examiner*—James J. Bell
*Attorney, Agent, or Firm*—Finnegan, Henderson Farabow, Garrett & Dunner

[57] ABSTRACT

An antimicrobially active, non-woven web, a wet wiper containing the web, and a method of making the web. The method includes the steps of forming an unbounded fibrous web; applying throughout the unbonded fibrous web an uncured binder and polyhexamethylene biguanide hydrochloride as an antimicrobial agent, the antimicrobial active agent being substantive to the fibers of the web and to the binder; and curing the binder material to bind the fibers together to form an antimicrobially active, non-woven web.

20 Claims, No Drawings

ANTIMICROBIALLY ACTIVE, NON-WOVEN WEB USED IN A WET WIPER

BACKGROUND OF THE INVENTION
1. Field of the Invention

The present invention relates to antimicrobially active nonwoven web incorporating polyhexamethylene biguanide hydrochloride as the antimicrobial in the web, to wet wipers containing such a web, and to a method of making a web.

2. Description of the Related Art

Wet wiper products, including those utilizing nonwoven and air-laid webs, require antimicrobial properties to destroy or inhibit the growth of various microorganisms, bacteria, yeast and molds. Several methods are known for treating the fabric of the web wiper product with an antimicrobial agent, but all suffer from various deficiencies.

Antimicrobial surface treatment of a fabric may be beneficial in the dry mode of usage, where microorganisms are either filtered out and/or killed upon contact with the surface of the fabric. U.S. Pat. No. 4,643,181 to Brown provides antimicrobial containing adhesive dressings, in which an antimicrobial agent such as polyhexamethylene biguanide hydrochloride is mixed with a solvent and applied to the outer, skin-contact portion of the adhesive. U.S. Pat. No. 4,655,756 to Fawkes disclosed a non-woven material superficially coated with a linear polymeric biguanide such as polyhexamethylene biguanide dihydrochloride. However, in the case of wet wipers, surface treatment of the fabric has been shown to be insufficient to obtain other necessary microbiological control. The liquid or lotion phase of the wet wiper product penetrates into the interstices of the fabric to carry the microorganisms past the treated surface into the interstices of the fabric, where they may grow and multiply.

Another disadvantage of the surface-treated wet wiper is that the antimicrobial agent leaches out from the fabric and leaves an irritating residue on the user's skin. Many individuals exhibit adverse reaction to such agents, and hence, their enjoyable use of the wet wiper product is significantly impeded.

To overcome these problems, an antimicrobially active nonwoven web for use in wet wipers was developed. (U.S. Pat. No. 4,615,937 and 4,692,374, both to Bouchette) The antimicrobial was applied to a binder which, in turn, was applied to an unbonded fibrous web so that the antimicrobial agent remained substantive to the fibers of the web and to the binder. The typical antimicrobial agent used was an organo-silicon quaternary ammonium salt, such as a silylquaternaryl ammonium salt.

However, it is an object of the present invention to provide an antimicrobially active non-woven web incorporating an antimicrobial agent that is substantive to the web and binder, which exhibits improved antimicrobial activity, a better rate of kill and improved efficacy at lower concentrations (i.e., lower than 0.25% by weight). It is also an object of this invention that the antimicrobial agent be substantive to the web and binder so that it does not leach out and cause irritation to users.

It is still another object of the present invention to provide an antimicrobially active wet wiper which demonstrates excellent aesthetic properties such as low tackiness and good wetting capabilities, and further, exhibits excellent stability and is substantially insensitive to chemical interference.

Additional objects and advantages of the invention will be set forth in the description which follows, and in part will be apparent from the description or may be learned by practice of the invention. The objects and advantages of the invention may be realized and obtained by means of the combinations particularly pointed out in the appended claims.

SUMMARY OF THE INVENTION

To achieve the foregoing objects, and in accordance with the purposes of the invention as embodied and broadly described herein, there is provided a method for making an antimicrobially active, non-woven web. The method comprises the steps of: (a) forming an unbonded fibrous web; (b) applying throughout the unbonded fibrous web an uncured binder and a polyhexamethylene biguanide hydrochloride as an antimicrobial agent, the polyhexamethylene biguanide hydrochloride being substantive to the fibers of the web and to the binder when the web is either wet or dry to prevent the antimicrobial agent from substantially diffusing from the fibers or binder and being present in an amount effective to act as an antimicrobial agent; and (c) curing the binder to bind the fibers together to form an antimicrobially active, non-woven web.

In addition, there is provided a method of making an antimicrobially active, air-laid non-woven web comprising the steps of: (a) air layering an unbonded cellulosic fiber web; (b) applying throughout the unbonded cellulosic fiber web an uncured polymeric binder and a polyhexamethylene biguanide hydrochloride as an antimicrobial agent, the polyhexamethylene biguanide hydrochloride being substantive to the cellulosic fibers of the web and to the polymeric binder when the web is either wet or dry; and (c) curing the binder to bind cellulosic fibers together to form an antimicrobially active, air-laid, non-woven web.

The antimicrobially active, non-woven web formed by the present invention comprises: (a) bonded fibers; (b) a binder distributed throughout the fibers, the binder being present in the amount effective to bind the fibers; and (c) polyhexamethylene biguanide hydrochloride being substantive to the fibers and the binder when the web is either wet or dry to present the polyhexamethylene biguanide hydrochloride from substantially diffusing from the fibers or binder and being present in an amount effective to act as an antimicrobial agent.

These non-woven webs can be used to form an antimicrobially active, wet wiper that comprises: (a) an antimicrobially active, non-woven web as defined above and (b) a substantially preservative free liquid in which the web is maintained in a wet condition until use.

The present invention overcomes the numerous inherent disadvantages commonly associated with previous antimicrobially active non-woven webs and obtains the various advantages of the invention. By substantively incorporating polyhexamethylene biguanide hydrochloride as the antimicrobial in the web and binder, and by no longer requiring the presence of a preservative in the surrounding solution, the non-woven web product of the present invention avoids leaving an irritating residue on the user's skin. Advantageously, the webs of the present invention containing polyhexamethylene biguanide hydrochloride do not experience substantial leaching out of the antimicrobial, they exhibit broad antimicrobial spectrum, they are effective at low concentrations, and they exhibit a fast rate of kill against United States Pharmacopeia (USP) organisms. Finally, the non-woven web products of the present invention have excellent aesthetic properties such as lower tack and good wetting capabilities and are also less irritating than the antimicrobially active non-woven webs of the prior art.

DESCRIPTION OF THE PREFERRED EMBODIMENTS

The method of the present invention produces an antimicrobially active, non-woven web. Initially, the present method forms an unbonded fibrous web. An uncured binder and polyhexamethylene biguanide hydrochloride as an antimicrobial agent are then applied throughout the unbonded fibrous web, with the antimicrobial agent being substantive to both the fibers of the web and to the binder when the web is either wet or dry. After application of the binder and the antimicrobial agent, the binder is cured to bind the fibers together to form an antimicrobially active non-woven web.

In accordance with the present invention, in the first step of the method, an unbonded fibrous web is formed. Although various cellulosic and synthetic fibers known in the art can be effectively used, the fibers are preferably cellulosic fibers and, more preferably, wood pulp fibers. The cellulosic fibers, such as wood pulp fibers, can be chemically treated and predried prior to forming, if desired. Examples of wood pulp fibers include various mechanical and chemical pulp fibers, such as cedar fibers, Southern pine fibers, spruce fibers, and hemlock fibers. The particular cellulosic fibers selected to make the non-woven web depend, in part, upon the type of texture, such as soft, woolly, or fluffy, and the porosity of the web that is desired. Alternatively, the fibers can be a combination of cellulosic and synthetic fibers.

The weight of the fibers, such as cellulosic fibers, used to form the unbonded fibrous web can vary depending upon the ultimate non-woven web that is produced. Typically, the weight of the fibers forming the web will vary within the range of about 5 lbs. per ream to about 60 lbs. per ream.

Various web forming techniques known in the art can be effectively used to form the unbonded fibers. The web can be formed by nonwoven techniques, such as air-laying the web or wet-laying the web. One type of apparatus for air forming fibers is shown in U.S. Pat. No. 4,292,271 to Buob et al. Other non-woven manufacturing techniques, such as melt blown, bonding, spun bonded, needle punched, and spun laced, may also be used along with the substantive antimicrobial agent to provide antimicrobially active webs. Some of the processing and cost benefits may be lost through the choice of these processes along with their concomitant raw materials limitations.

In accordance with the present invention, an uncured binder and polyhexamethylene biguanide hydrochloride as an antimicrobial agent are applied throughout the unbonded fibrous web with the antimicrobial agent being substantive to the fibers of the web and to the binder when the web is either wet or dry. Various binders known in the art can be used. A preferred binder is a polymeric binder, such as a latex binder. Acceptable latex binders include acrylate emulsions, butadiene-styrene emulsions, ethylene vinyl acetate emulsions and acrylonitrile-butadiene emulsions. An especially effective latex binder is ethylene vinyl acetate, which is sold under the trademark AIRFLEX A-410 by Air Products, Inc. of Allentown, Pa. The binder can also include a mixture of anionic and non-ionic binders, such as ethylene vinyl acetate, which is sold under the trademark AIRFLEX A-106 by Air Products, Inc. and ethylene acetate, sold under the trademark HA-8 by Rohm & Haas, of Philadelphia, Pa.

The amount of the binder that is to be applied to the fibers depends, in part, upon the type of fibers, such as cellulosic, which is to be used in conjunction with polyhexamethylene biguanide hydrochloride in the non-woven web. Typically, the amount of the binder applied to the fibers varies within the range of about 5% to about 30%. Similarly, the amount of solids in the binder, especially a latex binder, depends, inter alia, on the weight of the fibers in the non-woven web. Generally, latex binders having from about 5% to about 25% solids are used. It is permissible to add crosslinking agents to the binder such as an amelamine-formaldehyde crosslinking agent. Of course, the skilled artisan can select the particular binder, the amount of the binder used, and the amount of solids present in the binder depending upon, in part, the type of fibers that are to be bound. The binder is applied to the fibers by various techniques known in the art, such as spraying, foaming, or padding.

Polyhexamethylene biguanide hydrochloride is selected as antimicrobial agent to be substantive to both the fibers of the web and to the binder when the web is either wet or dry. As used herein, the polyhexamethylene biguanide hydrochloride is substantive if the polyhexamethylene biguanide hydrochloride attaches directly to the fibers of the web and to the binder without the need for an adhesive substance. Substantive antimicrobial agents do not substantially diffuse from the fibers or the binder used to bind the fibers together.

The polyhexamethylene biguanide hydrochloride is preferably applied to the fibrous web prior to or simultaneously with the application of the binder. Although various amounts of polyhexamethylene biguanide hydrochloride are applied to the web depending upon, in part, the fibers selected and the particular binder used, the amount of active polyhexamethylene biguanide hydrochloride is typically in the range of about 0.25% to about 3% of the total web weight.

The ionic character of the binder is carefully chosen so that the polyhexamethylene biguanide hydrochloride is usually substantially inert with respect to the binder to prevent ionic interaction of the antimicrobial agent and the binder.

The uncured binder and the polyhexamethylene biguanide hydrochloride are applied to the unbonded fibers in a manner that allows the binder and the polyhexamethylene biguanide hydrochloride to be present throughout the unbonded fibrous web and, hence, substantially uniformly distributed on the fibers. Accordingly, substantially all of the unbonded fibers of the web are to be contacted with the uncured binder and the polyhexamethylene biguanide hydrochloride during this application process.

Various application methods and apparatus, known in the art can be readily selected by the skilled artisan. For example, the uncured binder and the polyhexamethylene biguanide hydrochloride are sprayed onto unbound fibers, such as cellulosic fibers, that have been airlaid on a foraminous support. Similarly, the uncured binder and the polyhexamethylene biguanide hydrochloride can be contained in a bath through which the unbonded fibers pass. Other methods and apparatus include foaming and printing.

In accordance with the present invention, the binder material is cured to bind the fibers together to form an antimicrobial, non-woven web. Various curing techniques known in the art, such as infra-red radiation, electron beam, and forced hot air, can be effectively selected and used by the skilled artisan to achieve the proper degree of binder cure.

As a result, the present invention provides an antimicrobially active, non-woven web. The non-woven web has bonded fibers; a binder distributed throughout the fibers, the binder being present in an amount effective to bind the fibers; and polyhexamethylene biguanide hydrochloride-filling being substantive to the fibers and to the binder when the web is either wet or dry to prevent the polyhexamethylene biguanide hydrochloride from substantially diffusing from the fiber or the binder. The amount of polyhexamethylene biguanide hydrochloride present within the non-woven web is preferably in the range of about 0.25% to about 3% of the total web weight. The amount of the binder present within the non-woven web is preferably in the range of about 5% to about 30% of the total web weight.

When the antimicrobially active, non-woven web of the present invention is present in a substantially preservative free liquid, an antimicrobial active wet wiper is achieved. The substantially preservative free liquid, such as water, maintains the web in a wet condition until use. The governing criteria of wet wipers containing polyhexamethylene biguanide hydrochloride are substantivity, antimicrobial activity, and safety, such that the wet wiper is safe for use on human skin and eyes.

The following is an example of the present invention, and it is intended to be merely examplary.

EXAMPLE

An antimicrobially active, air-laid, non-woven web was prepared in accordance with the present invention. Unbonded cellulosic fibers were air-laid to produce an unbonded cellulosic fiber web of 40 pounds per ream. AIRFLEX 410, which is an acetate vinyl ethylene latex binder sold by Air Products, Inc. of Pennsylvania, and polyhexamethylene biguanide hydrochloride were applied through out the unbonded cellulosic fiber web as a combination of binder and antimicrobial agent. Upon application, the antimicrobial agent was substantive both to the cellulosic fibers of the web and to the binder when the web is either wet or dry. The binder was then cured to bind the cellulosic fibers together.

The resulting air-laid, non-woven web was tested to determine its antimicrobial activity. Specifically, the non-woven web was tested to determine its effect on reduction and inhibition of two United States Pharmacopeia (U.S.P.) antimicrobial preservative effectiveness challenge organisms and a third microorganism in a 28 day challenge test. The U.S.P. XX Preservative Effectiveness Test was modified to inoculate samples of the non-woven webs in the form of wet wiper towelettes. Those skilled in the art are readily familiar with the U.S.P. 28 day challenge test techniques and implications.

Basically, the wet wiper towelettes were subjected to an insult inoculation of two pathogenic microorganisms identified in the U.S.P. 28 day challenge test and a third microorganism: Asperqillus Niger (AN) and Staphylococcus aureus (SA) and Acetobactor Aceti (AA), with total inoculation levels of $10^5$ to $10^7$ microorganisms/ml. of the present invention. The microorganisms were plated on Day 1, Week 1, Week 2, Week 3 and Week 4, where the colony forming units per gram (cfu/g) were measured. The results of the 28 day challenge tests are provided in Table 1.

TABLE 1

|        | SIQUAT (cfu/g)      | PBH (cfu/g)         |
|--------|---------------------|---------------------|
| Day 1  |                     | 2                   |
| An     | $1.72 \times 10^5$  | $1.72 \times 10^5$  |
| Sa     | $5.53 \times 10^6$  | $5.32 \times 10^6$  |
| AA     | $1.97 \times 10^7$  | $1.97 \times 10^7$  |
| Week 1 |                     |                     |
| An     | $2 \times 10^4$     | $2 \times 10^5$     |
| Sa     | $<10$               | $<10$               |
| AA     | $9.7 \times 10^4$   | $<10$               |
| Week 2 |                     |                     |
| An     | $<10$               | $<10$               |
| Sa     | $<10$               | $<10$               |
| AA     | $<100$              | $<10$               |
| Week 3 |                     |                     |
| An     | $<10$               | $<10$               |
| Sa     | $<10$               | $<10$               |
| AA     | $<600$              | $<10$               |
| Week 4 |                     |                     |
| An     | $<10$               | $<10$               |
| Sa     | $<10$               | $<10$               |
| AA     | $<400$              | $<10$               |

The antimicrobial is considered effective in the product examined if: (a) the concentration of viable bacteria is reduced to not more than 0.1% of the initial concentrations by the fourteenth day; (b) the concentrations of viable yeasts and molds remain at or below the initial concentrations during the first fourteen days; and (c) the concentration of each test microorganism remains at or below these designated levels during the remainder of the 28 day test period.

The towelettes containing silyquaternaryl ammonium salt or polyhexamethylene biguanide hydrochloride reduced the three microorganisms in numbers by a factor of $10^4$ or more. However, the towelette containing polyhexamethylene biguanide hydrochloride exhibited superior activity against Acetobacter Aceti in comparison to the silylquaternaryl-containing towelette. The antimicrobial activity of the towelettes within the scope of the present invention were rated as being excellent.

Other embodiments of the invention will be apparent to one skilled in the art from a consideration of the specification or with the practice of the invention disclosed herein. It is intended that the specification and example be considered as exemplary only with the true scope and spirit of the invention being indicated by the claims.

What is claimed is:

1. A method for making an antimicrobially active, non-woven web comprising the steps of:
   (a) forming an unbounded fibrous web;
   (b) applying throughout the unbonded fibrous web an uncured binder and polyhexamethylene biguanide hydrochloride as an antimicrobial agent, the polyhexamethylene biguanide hydrochloride being substantive to the fibers of the web and to the binder when the web is either wet or dry to prevent the antimicrobial agent from substantially diffusing from the fibers or binder and being present in an amount effective to act as antimicrobial agent; and (c) curing the binder to bind the fibers together to form an antimicrobially active, non-woven web.

2. The method of claim 1, wherein the fibers are selected from the group consisting of cellulosic fibers, synthetic fibers, and combinations thereof.

3. The method of claim 1, wherein the binder is a polymeric binder.

4. The method of claim 3, wherein the polymeric binder is a latex binder.

5. The method of claim 1, wherein the amount of the polyhexamethylene biguanide hydrochloride applied to the web is in the range of about 0.25% to about 3% of the total web weight.

6. The method of claim 1, wherein the amount of the binder applied to the web is in the range of about 5% to about 30% of the total web weight.

7. The method of claim 1, wherein the unbonded fibrous web is formed by air-laying.

8. The method of claim 1, wherein the unbonded fibrous web is formed by wet-laying.

9. An antimicrobially active, wet wiper comprising:

(a) an antimicrobially active non-woven web comprising:
  (i) bonded fibers;
  (ii) a binder distributed throughout the fibers in an amount effective to bind the fibers;
  (iii) polyhexamethylene biguanide hydrochloride being substantive to the fibers and to the binder when the web is either wet or dry to prevent the polyhexamethylene biguanide hydrochloride from substantially diffusing from the fibers or the binder and being present in an amount effective to act as an antimicrobial agent; and (b) a substantially preservative free liquid in which the web is maintained in a wet condition until use.

10. The wet wiper of claim 9, wherein the fibers are selected from the group consisting of cellulosic fibers, synthetic fibers, and combinations thereof.

11. The wet wiper of claim 9, wherein the binder is a polymeric binder.

12. The wet wiper of claim 9, wherein the substantially preservative free liquid is water.

13. The wet wiper of claim 9, wherein the binder and the polyhexamethylene biguanide hydrochloride are substantially uniformly distributed on the fibers.

14. The wet wiper of claim 9, wherein the amount of the polyhexamethylene biguanide hydrochloride is in the range of about 0.25 to about 3% of the total web weight.

15. An antimicrobially active, non-woven web comprising:

(a) bonded fibers;
(b) a binder distributed throughout the fibers in an amount effective to bind the fibers; and
(c) polyhexamethylene biguanide hydrochloride being substantive to the fibers and to the binder when the web is either wet or dry to prevent the polyhexamethylene biguanide hydrochloride from substantially diffusing from the fibers or the binder and being present in about effective to act as an antimicrobial agent.

16. The web of claim 15, wherein binder and polyhexamethylene biguanide hydrochloride are substantially uniformly distributed on the fiber.

17. The web of claim 15, wherein the fibers are selected from the group consisting of cellulosic fibers, synthetic fibers, and combinations thereof.

18. The web of claim 15, wherein the binder is a polymeric binder.

19. The web of claim 15, wherein the amount of the polyhexamethylene biguanide hydrochloride is in the range of about 0.25% to about 3% of the total web weight.

20. The web of claim 15, wherein the amount of binder is in the range of about 5% to about 30% of the total web weight.

* * * * *

UNITED STATES PATENT AND TRADEMARK OFFICE
CERTIFICATE OF CORRECTION

PATENT NO.   : 4,837,079

DATED        : June 6, 1989

INVENTOR(S)  : THOMAS E. QUANTRILLE ET AL.

It is certified that error appears in the above-identified patent and that said Letters Patent is hereby corrected as shown below:

Claim 15, column 8, line 25, delete "about" and replace it with --an amount--.

Signed and Sealed this

Seventeenth Day of April, 1990

Attest:

HARRY F. MANBECK, JR.

*Attesting Officer*  *Commissioner of Patents and Trademarks*